US012697094B2

(12) United States Patent
Shimizu et al.

(10) Patent No.: US 12,697,094 B2
(45) Date of Patent: Aug. 4, 2026

(54) IMAGE DIAGNOSIS CATHETER

(71) Applicant: TERUMO KABUSHIKI KAISHA, Tokyo (JP)

(72) Inventors: Katsuhiko Shimizu, Fujinomiya (JP); Hiroyuki Ishihara, Tokyo (JP); Yasukazu Sakamoto, Hiratsuka (JP); Yoichiro Kuwano, Machida (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 839 days.

(21) Appl. No.: 17/484,972

(22) Filed: Sep. 24, 2021

(65) Prior Publication Data

US 2022/0008038 A1 Jan. 13, 2022

Related U.S. Application Data

(63) Continuation of application No. PCT/JP2020/012493, filed on Mar. 19, 2020.

(30) Foreign Application Priority Data

Mar. 27, 2019 (JP) ................................ 2019-061769

(51) Int. Cl.
A61B 8/00 (2006.01)
A61B 8/12 (2006.01)
(52) U.S. Cl.
CPC ................ *A61B 8/445* (2013.01); *A61B 8/12* (2013.01)
(58) Field of Classification Search
CPC ................................... A61B 8/12; A61B 8/445
See application file for complete search history.

(56) References Cited

U.S. PATENT DOCUMENTS 5,655,537 A    8/1997  Crowley
5,842,994 A  *  12/1998  TenHoff ................... A61B 8/12
                                                                600/468

(Continued)

FOREIGN PATENT DOCUMENTS

EP          2846698 A1     3/2015
JP          H0759776 A     3/1995

(Continued)

OTHER PUBLICATIONS

English Translations of the International Search Report (Form PCT/ISA/210) and the Written Opinion of the International Searching Authority (Form PCT/ISA/237) issued Jun. 2, 2020, by the Japanese Patent Office in corresponding International Application No. PCT/JP2020/012493. (7 pages).

(Continued)

*Primary Examiner* — Amelie R Davis
(74) *Attorney, Agent, or Firm* — Buchanan Ingersoll & Rooney PC

(57) ABSTRACT

An image diagnosis catheter is disclosed, which includes: a sheath inserted into a living body; an ultrasound vibrator capable of transmitting and receiving ultrasound in the sheath; a housing holding the ultrasound vibrator in the sheath; and a drive shaft attached to a proximal side of the housing and rotatable in the sheath, in which an ultrasound transmitting/receiving surface of the ultrasound vibrator facing a radial direction of the sheath is inclined with respect to an extension direction of the sheath such that a distal end of the ultrasound transmitting/receiving surface is closer to an inner peripheral surface of the sheath than a proximal end of the ultrasound transmitting/receiving surface, and the housing does not block a distal side of the ultrasound vibrator in an in-plane direction of the ultrasound transmitting/receiving surface.

7 Claims, 7 Drawing Sheets

(56)         References Cited

U.S. PATENT DOCUMENTS

| | | | |
|---|---|---|---|
| 6,074,349 | A | 6/2000 | Crowley |
| 2010/0152590 | A1 | 6/2010 | Moore et al. |
| 2010/0160788 | A1 | 6/2010 | Davies et al. |
| 2012/0123271 | A1 | 5/2012 | Cai |
| 2017/0042505 | A1* | 2/2017 | Havel .................. A61B 8/4461 |
| 2017/0079617 | A1 | 3/2017 | Yamamoto |
| 2019/0046159 | A1 | 2/2019 | Smith et al. |
| 2019/0133555 | A1 | 5/2019 | Hatakeyama |

FOREIGN PATENT DOCUMENTS

| | | | |
|---|---|---|---|
| JP | 2006223843 | A | 8/2006 |
| JP | 2016019737 | A | 2/2016 |
| JP | 2017056142 | A | 3/2017 |
| WO | 2013/170207 | A1 | 11/2013 |
| WO | 2017/199857 | A1 | 11/2017 |
| WO | 2019004355 | A1 | 1/2019 |

OTHER PUBLICATIONS

International Search Report (PCT/ISA/210) with translation and Written Opinion (PCT/ISA/237) mailed on Jun. 2, 2020, by the Japan Patent Office as the International Searching Authority for International Application No. PCT/JP2020/012493.
Office Action (Examination report No. 1 for standard patent application) issued on Nov. 27, 2024, in corresponding Australian Patent Application No. 2023237114. (3 pages).

* cited by examiner

IMAGE DIAGNOSIS CATHETER

CROSS-REFERENCES TO RELATED APPLICATIONS

This application is a continuation of International Application No. PCT/JP2020/012493 filed on Mar. 19, 2020, which claims priority to Japanese Patent Application No. 2019-061769 filed on Mar. 27, 2019, the entire content of both of which is incorporated herein by reference.

FIELD OF THE DISCLOSURE

The present disclosure generally relates to an image diagnosis catheter.

BACKGROUND DISCUSSION

Imaging diagnosis catheters, which obtain an image by an intravascular ultrasound (IVUS) method are known as an image diagnosis catheter, which can obtain a tomographic image of a blood vessel or the like. Japanese Patent Application Publication No. 2017-56142 A describes this type of image diagnosis catheter.

The image diagnosis catheter described in Japanese Patent Application Publication No. 2017-56142 A can generate a tomographic image of a relatively thin tube such as a blood vessel. It is also conceivable that the image diagnosis catheter described in Japanese Patent Application Publication No. 2017-56142 A can be used in, for example, a heart chamber. However, the space of the heart chamber is relatively larger than that of the blood vessel, and thus it is necessary to increase the output of ultrasound in order to obtain a clear tomographic image of the heart chamber. It has been discovered that a non-target object is easily reflected as noise in a tomographic image as a result of an increase in ultrasound output.

SUMMARY

An image diagnosis catheter is disclosed that is capable of suppressing the reflection of a non-target object as noise in a tomographic image.

An image diagnosis catheter as a first aspect of the disclosure includes: a sheath inserted into a living body; an ultrasound vibrator configured to transmit and receive ultrasound in the sheath; a housing holding the ultrasound vibrator in the sheath; and a drive shaft attached to a proximal side of the housing and rotatable in the sheath, in which an ultrasound transmitting/receiving surface of the ultrasound vibrator facing a radial direction of the sheath is inclined with respect to an extension direction of the sheath such that a distal end of the ultrasound transmitting/receiving surface is closer to an inner peripheral surface of the sheath than a proximal end of the ultrasound transmitting/receiving surface, and the housing does not block a distal side of the ultrasound vibrator in an in-plane direction of the ultrasound transmitting/receiving surface.

As an embodiment of the disclosure, a distal end of the housing is not positioned distal to a distal end of the ultrasound vibrator, or the housing is positioned distal to the distal end of the ultrasound vibrator and only on a back surface side of the ultrasound transmitting/receiving surface of the ultrasound vibrator.

As an embodiment of the disclosure, a distal end surface of the ultrasound vibrator includes a curved surface.

As an embodiment of the disclosure, the housing includes a proximal tubular portion disposed coaxially with the drive shaft and a protruding portion distally protruding from the proximal tubular portion and positioned on a back surface side of the ultrasound transmitting/receiving surface of the ultrasound vibrator.

As an embodiment of the disclosure, a distal end of the protruding portion is not positioned distal to a distal end of the ultrasound vibrator, or the protruding portion is positioned distal to the distal end of the ultrasound vibrator and only on a back surface side of the ultrasound transmitting/receiving surface of the ultrasound vibrator.

As an embodiment of the disclosure, the protruding portion is positioned below a central axis of the proximal tubular portion in a case where a side faced by the ultrasound transmitting/receiving surface is an upper side and a lower side is opposite to the upper side.

The image diagnosis catheter as an embodiment of the disclosure includes a backing member positioned between the protruding portion and the ultrasound vibrator and supporting the ultrasound vibrator from the back surface side of the ultrasound transmitting/receiving surface.

As an embodiment of the disclosure, the protruding portion is a concave plate portion curved in a circular arc shape in a cross section in a direction orthogonal to a central axis direction of the proximal tubular portion, and at least a part of the backing member is positioned in a concave portion of the concave plate portion.

As an embodiment of the disclosure, the backing member includes a distal cover portion covering a distal end surface of the ultrasound vibrator.

As an embodiment of the disclosure, the housing does not cover a side end surface of the ultrasound vibrator, and the side end surface of the ultrasound vibrator includes a curved surface.

As an embodiment of the disclosure, the backing member contains a scattering agent configured to scatter an ultrasound wave.

As an embodiment of the disclosure, a position of the ultrasound vibrator is radially inside an outer peripheral surface of the proximal tubular portion.

According to the disclosure, an image diagnosis catheter having a configuration capable of suppressing the reflection of a non-target object as noise in a tomographic image can be provided.

In accordance with an aspect, an imaging catheter is disclosed comprising: an elongated sheath configured to be inserted into a living body; an imaging core unit disposed in the sheath; a drive shaft attached to a proximal end of the imaging core unit and disposed in the sheath; the imaging core unit comprising: an ultrasound vibrator that includes an ultrasound transmitting/receiving surface and a back surface opposed to the ultrasound transmitting/receiving surface; and a supporting member that supports the back surface of the ultrasound vibrator, wherein the driving shaft is movable with the imaging core unit in the sheath along an extension direction of the sheath and rotatable with the imaging core unit in the sheath around an axis of the sheath; and wherein the supporting member does not block a distal side of the ultrasound vibrator in an in-plane direction of the ultrasound transmitting/receiving surface.

In accordance with another aspect, an image diagnosis catheter is disclosed comprising: an elongated sheath configured to be inserted into a living body; an imaging core unit disposed in the sheath; a drive shaft attached to a proximal end of the imaging core unit and disposed in the sheath; the imaging core unit including: an ultrasound vibrator that includes an ultrasound transmitting/receiving surface and a back surface opposed to the ultrasound transmitting/receiving surface; a backing member that supports the back surface of the ultrasound vibrator and configured to absorb a partial ultrasound transmitted from the ultrasound vibrator; and a supporting member that supports the back surface of the ultrasound vibrator via the backing member; wherein the driving shaft is movable with the imaging core unit in the sheath along an extension direction of the sheath and rotatable with the imaging core unit in the sheath around an axis of the sheath; and wherein the backing member includes a distal cover portion covering a distal end surface of the ultrasound vibrator.

BRIEF DESCRIPTION OF THE DRAWINGS

FIG. 7A is a side view of the imaging core unit. FIG. 7B is a top view of the imaging core unit.

DETAILED DESCRIPTION

Figure 1:
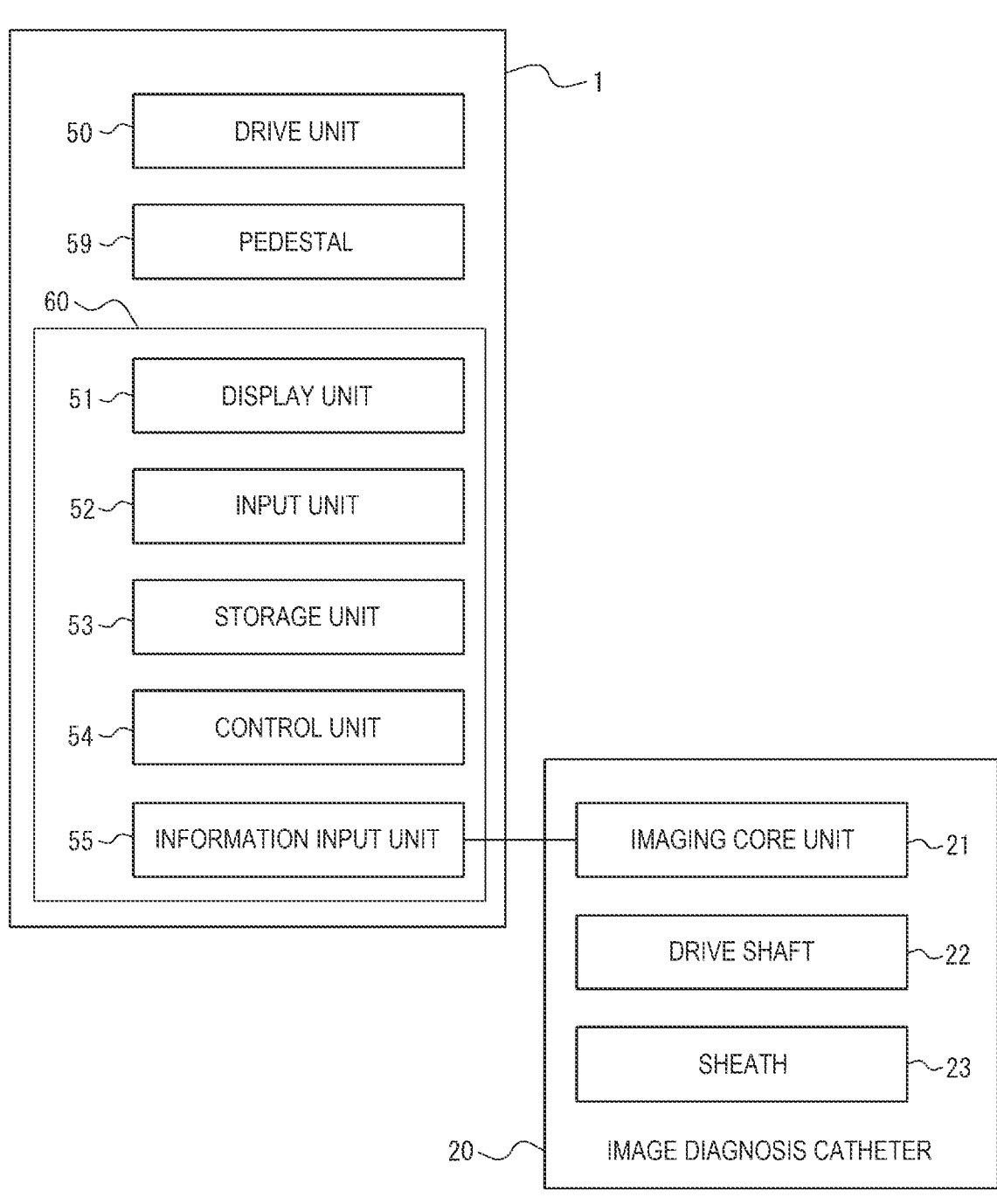
FIG. 1 is a block diagram illustrating a schematic configuration of an image diagnosis catheter as an embodiment of the disclosure and an image processing device to which the image diagnosis catheter is connected.

Set forth below with reference to the accompanying drawings is a detailed description of embodiments of an image diagnosis catheter representing examples of the inventive image diagnosis catheter disclosed here. The same reference numerals are used for common members and parts in the drawings. In addition, in the present specification, the side of the image diagnosis catheter according to the disclosure that is inserted into an organ or the like is "distal side" or "tip side" and the hand side that is operated is "proximal side" or "base end side". Further, the extension direction of a sheath of the image diagnosis catheter according to the disclosure is referred to as "extension direction A", the circumferential direction of the sheath of the image diagnosis catheter according to the disclosure is referred to as "circumferential direction B", and the radial direction of the sheath of the image diagnosis catheter according to the disclosure is referred to as "radial direction C".

Figure 2:
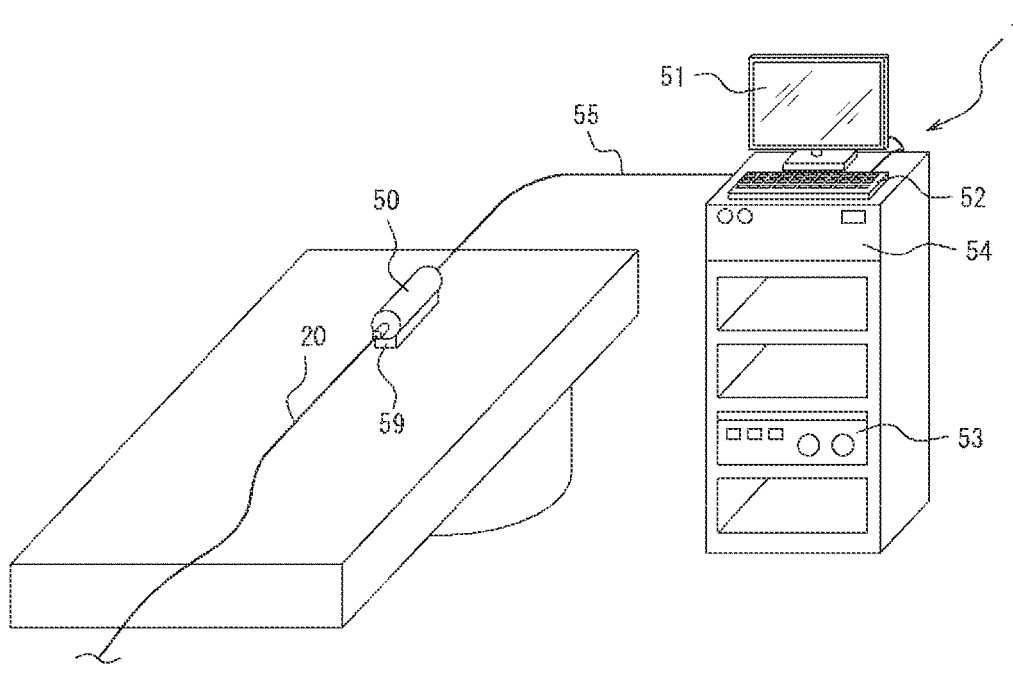
FIG. 2 is a schematic view illustrating a state where the image diagnosis catheter and the image processing device illustrated in FIG. 1 are connected.

FIG. 1 is a block diagram illustrating a schematic configuration of an image diagnosis catheter 20 as an embodiment of the image diagnosis catheter according to the disclosure and an image processing device 1 to which the image diagnosis catheter 20 is connected. FIG. 2 is a schematic view illustrating a state where the image diagno-

Figure 3:
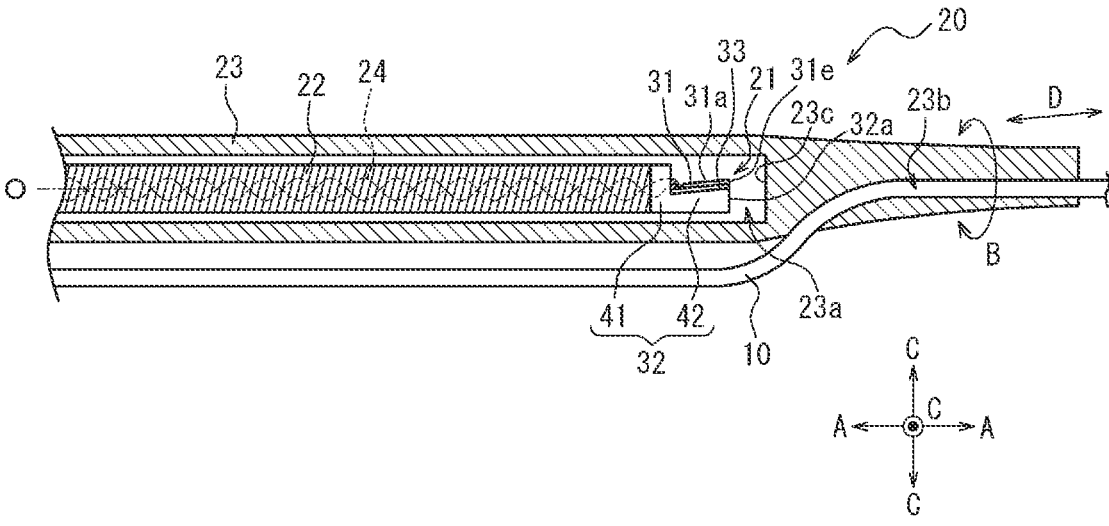
FIG. 3 is a cross-sectional view illustrating a distal-side end portion of the image diagnosis catheter illustrated in FIG. 2.

4 sis catheter 20 and the image processing device 1 are connected. FIG. 3 is a cross-sectional view illustrating a distal-side end portion of the image diagnosis catheter 20.

As illustrated in FIGS. 1 and 2 the image processing device 1 includes a drive unit 50, a pedestal 59, and an image processing unit 60. The image processing unit 60 includes a display unit 51, an input unit 52, a storage unit 53, a control unit 54, and an information input unit 55. The image processing unit 60 generates a tomographic image based on information on an organ, a blood vessel, or a medical instrument acquired by an imaging core unit 21 (described later) of the image diagnosis catheter 20 inserted into a living body.

As illustrated in FIGS. 1 and 3, the image diagnosis catheter 20 includes the imaging core unit 21, a drive shaft 22, and a sheath 23. The information input unit 55 of the image processing device 1 is electrically connected to the imaging core unit 21 of the image diagnosis catheter 20.

The imaging core unit 21 acquires information on a blood vessel or an organ such as the heart (hereinafter, appropriately referred to as "organ or the like") or a medical instrument positioned in the organ or the like. Specifically, the imaging core unit 21 includes an ultrasound vibrator 31. The ultrasound vibrator 31 of the imaging core unit 21 transmits ultrasound toward the organ or the like or the medical instrument positioned in the organ or the like and receives the ultrasound reflected from the organ or the like or the medical instrument. The image processing device 1 generates a tomographic image of the organ or the like or the medical instrument based on the ultrasound information received by the ultrasound vibrator 31 of the imaging core unit 21 via the information input unit 55. Further, the image processing device 1 may generate and display a three-dimensional image of the organ or the like or the medical instrument based on a plurality of sequentially generated tomographic images.

The drive unit 50 incorporates a motor and is connected to the drive shaft 22 of the image diagnosis catheter 20. As illustrated in FIG. 3, the imaging core unit 21 is attached to the distal side of the drive shaft 22. Accordingly, the rotational drive force of the drive unit 50 is transmitted to the imaging core unit 21 via the drive shaft 22. As a result, the imaging core unit 21 is rotatable in the circumferential direction B in the sheath 23 (described later).

In addition, as illustrated in FIG. 2, the drive unit 50 is attached to the pedestal 59 so as to be slidable. The image diagnosis catheter 20 is connected to the drive unit 50 attached to the pedestal 59. The drive unit 50 is capable of moving along the extension direction A with respect to the pedestal 59. Accordingly, the drive shaft 22 connected to the drive unit 50 moves along the extension direction A together with the drive unit 50. As a result, the imaging core unit 21 attached to the distal side of the drive shaft 22 also follows the drive shaft 22 and moves along the extension direction A in the sheath 23.

The display unit 51 displays and outputs the display information generated by the control unit 54. The display unit 51 can include a display device such as a liquid crystal display and an organic EL display.

The input unit 52 receives the input of information or an instruction from an operator and outputs the received input information or input instruction to the control unit 54. The input unit 52 can include an input device such as a keyboard, a mouse, and a touch panel. In a case where the input unit 52 includes a touch panel, the touch panel may be provided integrally with the display unit 51.

The storage unit 53 stores various programs and information for causing the control unit 54 to execute a specific function. In addition, the storage unit 53 stores a tomographic image of the organ or the like of a subject generated by the control unit 54. The storage unit 53 can include a storage device such as a RAM and a ROM.

The control unit 54 controls the operation of each component constituting the image processing device 1. The control unit 54 executes a specific function by reading a specific program. The control unit 54 can include, for example, a processor.

The information input unit 55 receives the input of the ultrasound information on, for example, the organ or the like or the medical instrument positioned in the organ or the like acquired by the imaging core unit 21. Specifically, the information input unit 55 is electrically connected to the imaging core unit 21 via a signal line 24 extending in the drive shaft 22, acquires a signal related to the ultrasound information acquired by the imaging core unit 21, and transmits the signal to the control unit 54. The control unit 54 generates a tomographic image including the organ or the like and the medical instrument positioned in the organ or the like based on the input information.

As illustrated in FIG. 3, the imaging core unit 21 includes the ultrasound vibrator 31 capable of transmitting and receiving ultrasound in the sheath 23 and a housing 32 holding the ultrasound vibrator 31 in the sheath 23.

As illustrated in FIG. 3, the ultrasound vibrator 31 includes an ultrasound transmitting/receiving surface 31a capable of transmitting and receiving ultrasound. The ultrasound transmitting/receiving surface 31a faces the radial direction C. Thus, the ultrasound vibrator 31 transmits ultrasound mainly toward the radial direction C from the ultrasound transmitting/receiving surface 31a Further, the ultrasound transmitting/receiving surface 31a is inclined with respect to the extension direction A such that the distal end of the ultrasound transmitting/receiving surface 31a is closer to the inner peripheral surface of the sheath 23 than the proximal end of the ultrasound transmitting/receiving surface 31a.

The ultrasound vibrator 31 transmits ultrasound toward a target part and receives the ultrasound reflected from the target part. Information such as the distance to the target part is acquired based on the time from the ultrasound transmission to the reception.

As illustrated in FIG. 3, the housing 32 holds the ultrasound vibrator 31. In addition, the housing 32 does not block the distal side of the ultrasound vibrator 31 in an in-plane direction D of the ultrasound transmitting/receiving surface 31a. "In-plane direction of the ultrasound transmitting/receiving surface" means any direction parallel to the ultrasound transmitting/receiving surface. More specifically, a distal end 32a of the housing 32 of the present embodiment is not positioned distal to a distal end 31e of the ultrasound vibrator 31.

The drive shaft 22 is attached to the proximal side of the housing 32 of the imaging core unit 21. In addition, the proximal-side end portion of the drive shaft 22 is connected to the drive unit 50 described above. The drive shaft 22 can be configured by, for example, a multi-layer coil having different winding directions around an axis. Examples of the material for the multi-layer coil can include, for example, stainless steel and a nickel-titanium (Ni—Ti) alloy.

The sheath 23 is a flexible tubular member covering the outer sides of the imaging core unit 21 and the drive shaft 22 in the radial direction C. In the present embodiment, the sheath 23 partitions a first lumen 23a where the imaging core unit 21 and the drive shaft 22 are accommodated. In addition, the sheath 23 partitions a second lumen 23b into which a guide wire 10 can be inserted as well as the first lumen 23a. FIG. 3 illustrates a state where the imaging core unit 21 and the drive shaft 22 are accommodated in the first lumen 23a and the guide wire 10 is inserted in the second lumen 23b. The image diagnosis catheter 20 is inserted into the organ or the like along the guide wire 10. Although the sheath 23 of the present embodiment is a rapid exchange-type (RX-type) sheath in which the second lumen 23b is partitioned only in the distal end portion, the sheath 23 is not limited to the RX-type sheath and may be, for example, an over-the-wire-type (OTW-type) sheath.

The distal end of the first lumen 23a of the sheath 23 is completely closed by a wall portion 23c. However, the distal end of the first lumen 23a of the sheath 23 is not limited to a completely closed configuration and may be provided with a wall portion communicating with the outside and having a through hole smaller in cross-sectional area than the first lumen 23a.

The sheath 23 can be formed of a flexible material. The specific material for the sheath 23 is not particularly limited. For example, the material for the sheath 23 can include various thermoplastic elastomers such as styrene-based, polyolefin-based, polyurethane-based, polyester-based, polyamide-based, polyimide-based, polybutadiene-based; transpolyisoprene-based; fluororubber-based, and chlorinated polyethylene-based, and the examples of the material of the sheath 23 can also include one or more of the above-mentioned materials being combined (for example, polymer alloy, polymer blend, laminate, etc.).

Figure 4:
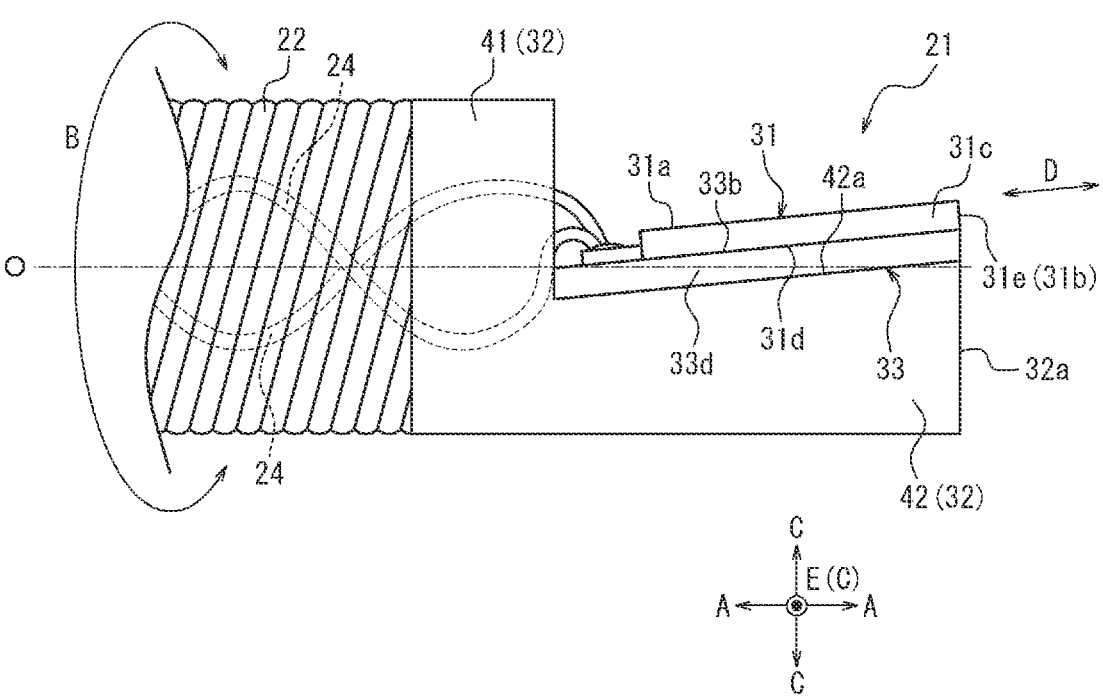
FIG. 4 is a side view of an imaging unit illustrated in FIG. 3.
Figure 5:
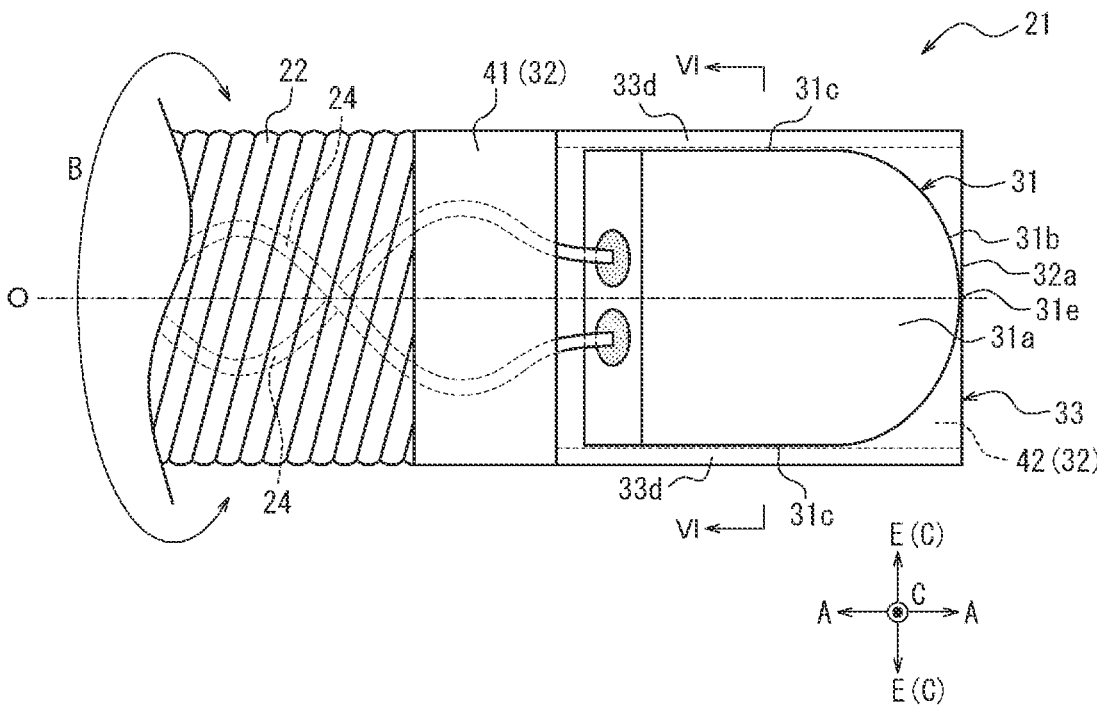
FIG. 5 is a top view of the imaging unit illustrated in FIG. 3.
Figure 6:
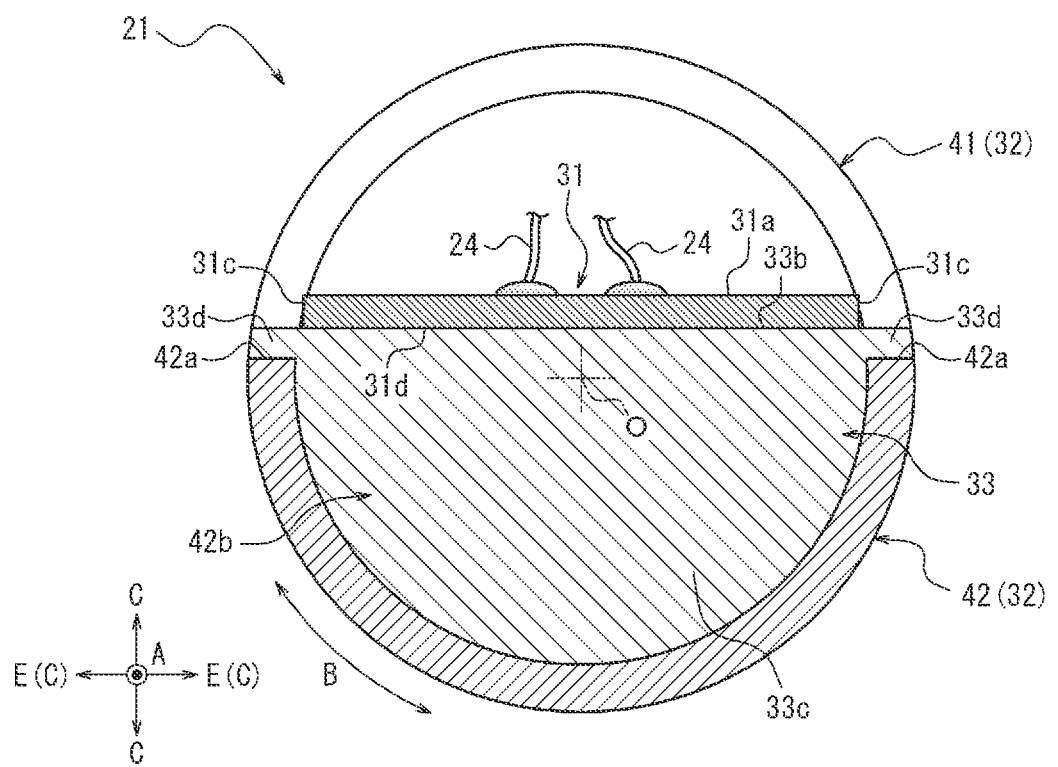
FIG. 6 is a cross-sectional view taken along line VI-VI of FIG. 5.

Next, the imaging core unit 21 of the image diagnosis catheter 20 will be described in more detail. FIG. 4 is a side view of the imaging core unit 21. FIG. 5 is a top view of the imaging core unit 21. FIG. 6 is a cross-sectional view taken along line VI-VI of FIG. 5. Here, the side view of the imaging core unit 21 of the present embodiment means a plan view seen from a point of view where the ultrasound transmitting/receiving surface 31a looks linear. In addition, the top view of the imaging core unit 21 of the present embodiment means a plan view in which the imaging core unit 21 is viewed from the ultrasound transmitting/receiving surface 31a side.

As described above, the imaging core unit 21 includes the ultrasound vibrator 31 and the housing 32. As illustrated in FIGS. 3 and 4, the ultrasound transmitting/receiving surface 31a of the ultrasound vibrator 31 is inclined with respect to the extension direction A such that the distal end of the ultrasound transmitting/receiving surface 31a is closer to the inner peripheral surface of the sheath 23 than the proximal end of the ultrasound transmitting/receiving surface 31a.

The ultrasound vibrator 31 may transmit ultrasound from a surface other than the ultrasound transmitting/receiving surface 31a in a case where, for example, the output of ultrasound is increased. In such a case, the ultrasound transmitted from a distal end surface 31b of the ultrasound vibrator 31 may be reflected by the wall portion 23c on the distal side of the first lumen 23a of the sheath 23 and received by the ultrasound transmitting/receiving surface 31a. As a result, there may be a problem that the wall portion 23c of the sheath 23, which is a non-target object, is reflected as noise in a tomographic image.

However, the ultrasound transmitting/receiving surface 31a of the ultrasound vibrator 31 is inclined with respect to the extension direction A such that the distal end of the ultrasound transmitting/receiving surface 31a is closer to the inner peripheral surface of the sheath 23 than the proximal end of the ultrasound transmitting/receiving surface 31a. Accordingly, even if ultrasound is transmitted from the distal end surface 31b of the ultrasound vibrator 31, it is difficult for the ultrasound to reach the wall portion 23c on the distal side of the first lumen 23a of the sheath 23 as compared with a configuration in which the ultrasound transmitting/receiving surface is parallel to the extension direction A of the sheath. In addition, even if the ultrasound reaches the wall portion 23c on the distal side of the first lumen 23a of the sheath 23 and is reflected, it becomes rather difficult for the ultrasound transmitting/receiving surface 31a to receive the ultrasound reflected from the wall portion 23c on the distal side of the first lumen 23a of the sheath 23 since the ultrasound transmitting/receiving surface 31a is inclined so as to face the proximal side. Accordingly, the reflection of the wall portion 23c of the sheath 23, which is a non-target object, as noise in a tomographic image can be suppressed.

Although the angle of the ultrasound transmitting/receiving surface 31a with respect to the extension direction A is not particularly limited, the angle can be, for example, preferably 5 degrees to 15 degrees, and more preferably 7 degrees to 12 degrees.

Further, as illustrated in FIGS. 3 and 4, the housing 32 does not block the distal side of the ultrasound vibrator 31 in the in-plane direction D of the ultrasound transmitting/receiving surface 31a. More specifically, the distal end 32a of the housing 32 of the present embodiment is not positioned distal to the distal end 31e of the ultrasound vibrator 31. Although the position of the distal end 32a of the housing 32 substantially coincides with the position of the distal end 31e of the ultrasound vibrator 31 in the extension direction A in the present embodiment, the disclosure is not limited to this configuration. The distal end 32a of the housing 32 may be positioned proximal to the distal end 31e of the ultrasound vibrator 31.

By the housing 32 having such a configuration, the ultrasound transmitted from the ultrasound transmitting/receiving surface 31a and the distal end surface 31b of the ultrasound vibrator 31 being reflected by the housing 32 as a non-target object and received by the ultrasound transmitting/receiving surface 31a as ultrasound noise can be suppressed. Thus, the reflection of the housing 32, which is a non-target object, as noise in a tomographic image can be suppressed.

Figure 7A:
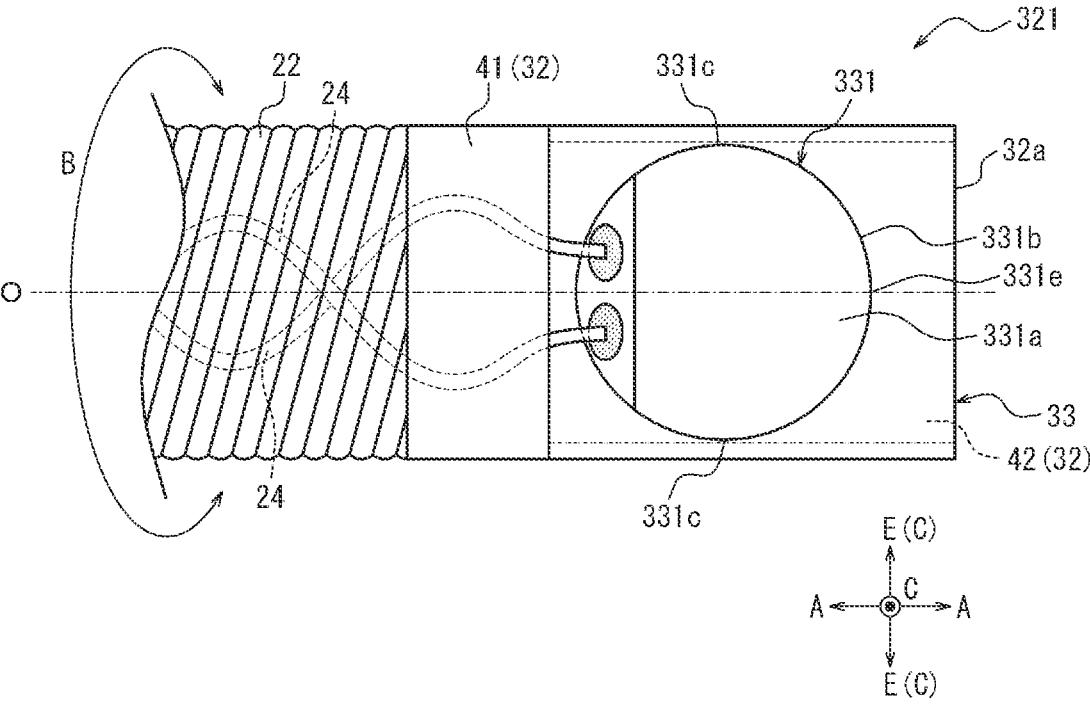
FIGS. 7A and 7B are diagrams illustrating a modification example of an imaging core unit illustrated in FIG. 3.
Figure 7B:
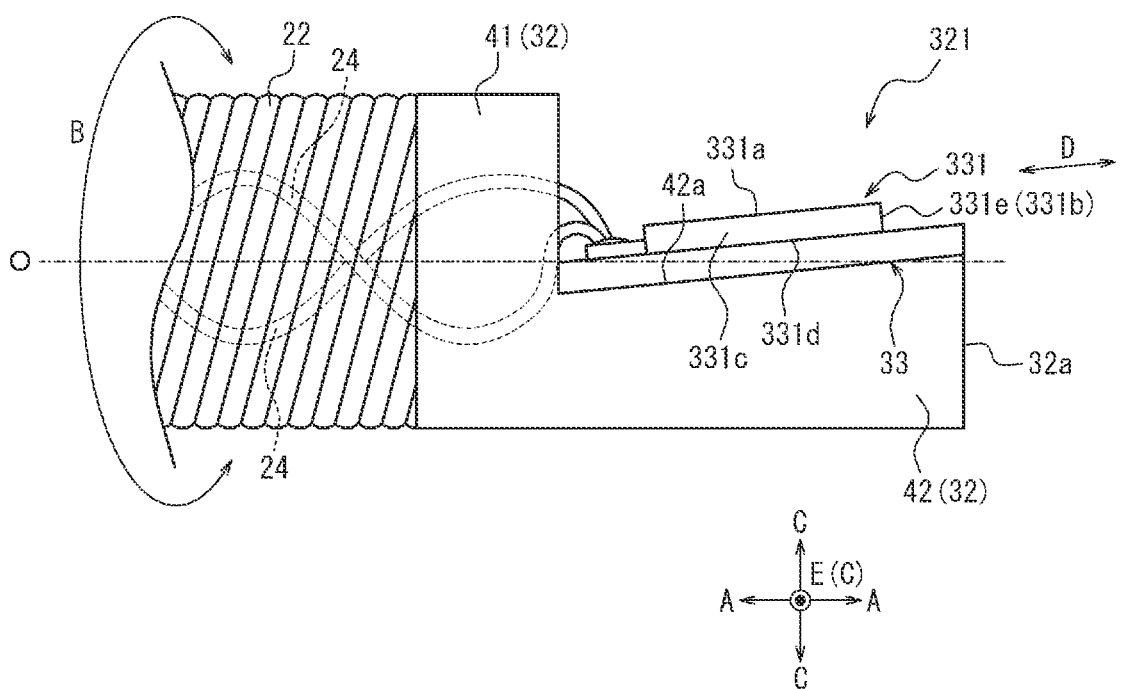

However, the housing may be positioned distal to the distal end of the ultrasound vibrator and only on the back surface side of the ultrasound transmitting/receiving surface of the ultrasound vibrator (see FIGS. 7A and 7B). Even with such a housing, the same effect as described above can be obtained.

As described above, according to the imaging core unit 21 illustrated in FIGS. 3 and 4, the ultrasound vibrator 31 receiving ultrasound that becomes noise from the distal side of the ultrasound transmitting/receiving surface 31a in the in-plane direction D can be suppressed. Thus, the reflection of a non-target object as noise in a tomographic image can be suppressed.

Further, as illustrated in FIG. 5, the distal end surface 31b of the ultrasound vibrator 31 of the present embodiment includes a curved surface. In this manner, the traveling direction of the ultrasound transmitted from the ultrasound vibrator 31 can be dispersed. Thus, it becomes difficult for the ultrasound transmitted from the distal end surface 31b of the ultrasound vibrator 31 to reach the wall portion 23c of the sheath 23. As a result, the reflection of the wall portion 23c of the sheath 23, which is a non-target object, as noise in a tomographic image can be suppressed.

The distal end surface 31b of the present embodiment is a surface substantially orthogonal to the ultrasound transmitting/receiving surface 31a. In addition, the distal end surface 31b of the present embodiment is a convex surface curved in a circular arc shape in the top view illustrated in FIG. 5. However, the shape of the curved surface of the distal end surface 31b is not limited to the shape according to the present embodiment. The distal end surface 31b may be, for example, a surface inclined with respect to the ultrasound transmitting/receiving surface 31a in the side view illustrated in FIG. 4 or curved in the side view illustrated in FIG. 4. In addition, the distal end surface 31b may be uneven. However, the distal end surface 31b is preferably a surface substantially orthogonal to the ultrasound transmitting/receiving surface 31a and a convex curved surface curved in the top view illustrated in FIG. 5 as in the present embodiment. In this manner, t is rather easy to secure the wide ultrasound transmitting/receiving surface 31a and it is also rather easy to increase ultrasound output. Examples of the top-view shape of the ultrasound vibrator provided with the distal end surface including such a curved surface include a circular shape, an elliptical shape, and a key-hole shaped mound shape.

In addition, in the ultrasound vibrator 31, ultrasound may be transmitted from a side end surface 310 as well as the distal end surface 31b. The side end surface 31c is an end surface in a direction orthogonal to the extension direction A. Accordingly, the side end surface 310 of the ultrasound vibrator 31 of the present embodiment is configured by a plane linearly extending in the top view illustrated in FIG. 5, and the side end surface preferably includes, for example, a curved surface. In this manner, it becomes rather difficult for a tomographic image to reflect ultrasound noise attributable to ultrasound transmitted from the side end surface as in the case of the distal end surface 31b described above. FIGS. 7A and 7B are diagrams illustrating an imaging core unit 321 as a modification example of the imaging core unit 21 of the present embodiment. FIG. 7A is a side view of the imaging core unit 321. FIG. 7B is a top view of the imaging core unit 321. The housing 32 illustrated in FIGS. 7A and 7B does not cover a side end surface 331c of an ultrasound vibrator 331. In addition, the side end surface 331c of the ultrasound vibrator 331 includes a curved surface. More specifically, in the ultrasound vibrator 331 illustrated in FIGS. 7A and 73, a distal end surface 331b and the side end surface 331c constitute a series of continuous circular arc shapes in the top view (see FIG. 7B). The shape of the side end surface 331c is not limited to the shape illustrated in FIGS. 7A and 7B. However, for the same reason as the distal end surface 31b (see FIG. 5) of the ultrasound vibrator 31 described above, the side end surface is preferably a surface substantially orthogonal to an ultrasound transmitting/receiving surface 331a and a convex curved surface curved in a top view as in the case of the side end surface 331c illustrated in FIGS. 7A and 7B.

However, preferable from the viewpoint of the straightness of the ultrasound of the ultrasound vibrator is the side end surface 31c illustrated in FIG. 5, which is configured by a plane linearly extending in the top view. Further, from the viewpoint of the straightness of the ultrasound of the ultrasound vibrator, it is preferable that the distal end surface is also configured by a plane linearly extending in a top view.

In addition, the housing 32 of the imaging core unit 321 illustrated in FIGS. 7A and 7B is positioned distal to a distal end 331e of the ultrasound vibrator 331 and only on the back surface 331d side of the ultrasound transmitting/receiving surface 331a of the ultrasound vibrator 331. Accordingly, the reflection of the housing 32 as noise in a tomographic image can be suppressed.

In the present embodiment, the imaging core unit 21 will be described in more detail with reference to FIGS. 3 to 6.

The imaging core unit 21 of the present embodiment includes a backing member 33 in addition to the ultrasound vibrator 31 and the housing 32 described above.

The ultrasound vibrator 31 of the present embodiment includes a piezoelectric element and an acoustic matching member. The piezoelectric element includes a flat piezoelectric body, a first electrode laminated on at least one side of the piezoelectric body in the thickness direction, and a second electrode laminated on at least the other side of the piezoelectric body in the thickness direction.

The piezoelectric body of the piezoelectric element is configured by, for example, a piezoelectric ceramic sheet. Examples of the material for the piezoelectric ceramic sheet can include piezoelectric ceramic materials such as lead zirconate titanate (PZT) and lithium niobate. The piezoelectric body may be formed of rock crystal instead of the piezoelectric ceramic material.

The first electrode and the second electrode of the piezoelectric element can be formed by, for example, being respectively laminated as electrode layers on both surfaces of the piezoelectric body in the thickness direction by a sputtering method, a vapor deposition method, or an ion plating method using a mask material. Examples of the materials for the first electrode and the second electrode include metals such as silver, chromium, copper, nickel, and gold and laminates of the metals.

In accordance with an exemplary embodiment, one of the first electrode and the second electrode of the present embodiment is configured by a folded electrode. Accordingly, as illustrated in FIG. 5, the signal line 24 is electrically connected to each of the first electrode and the second electrode only on one side of the piezoelectric element in the thickness direction. However, the first electrode and the second electrode may be ordinary electrodes respectively positioned only on both sides of the piezoelectric element in the thickness direction.

The acoustic matching member is laminated on one side of the piezoelectric element in the thickness direction. By the acoustic matching member being provided, the efficiency of ultrasound propagation to a subject can be enhanced. Thus, the acoustic matching member constitutes an acoustic matching layer enhancing the relatively efficiency of ultrasound propagation. The ultrasound transmitting/receiving surface 31a of the present embodiment is configured by the acoustic snatching member.

The acoustic matching layer as an acoustic matching member can be formed by, for example, a method by which a sheet material forming an acoustic matching layer is bonded to a piezoelectric element or a method by which a liquid acoustic matching material forming an acoustic matching layer is applied and cured. Examples of the material for the acoustic matching member can include a resin material such as epoxy resin. In addition, the acoustic matching member may be configured by a laminate of resin layers made of a resin material.

The ultrasound vibrator 31 of the present embodiment is formed by a convex curved surface being applied to a rectangular plate-shaped distal-side surface, for example, of 1.5 mm to 2.5 mm in a top view. The above-described ultrasound vibrator 331 illustrated in FIGS. 7A and 7B has an outer diameter, for example, of 1.5 mm to 2.5 mm in a top view. In addition, the output frequency of the ultrasound transmitted from the ultrasound vibrator 31 (see FIG. 5 and so on) and the ultrasound vibrator 331 (see FIGS. 7A and 7B) is, for example, 7 MHz to 20 MHz. In addition, the transmission voltage of the ultrasound transmitted from the ultrasound vibrator 31 (see FIG. 5 and so on) and the ultrasound vibrator 331 (see FIGS. 7A and 7B) is, for example, 10 Vp-p to 100 Vp-p.

The housing 32 of the present embodiment includes a proximal tubular portion 41 disposed coaxially with the drive shaft 22 and a protruding portion 42 distally protruding from the proximal tubular portion 41 and positioned on the back surface 31d side of the ultrasound transmitting/receiving surface 31a of the ultrasound vibrator 31. With such a configuration, a configuration in which the housing 32 does not block the distal side of the ultrasound vibrator 31 in the in-plane direction D of the ultrasound transmitting/receiving surface 31a can be realized by means of the housing 32, which has a relatively simple shape.

More specifically, the distal end 32a of the housing 32 of the present embodiment is the distal end of the protruding portion 42. Accordingly, as illustrated in FIGS. 3 and 4, the distal end of the protruding portion 42 in the present embodiment is not positioned distal to the distal end 31e of the ultrasound vibrator 31. In this manner, according to the housing 32 of the present embodiment, a configuration in which the distal side of the ultrasound vibrator 31 is not blocked in the in-plane direction D of the ultrasound transmitting/receiving surface 31a can be realized by means of a simple configuration. Particularly preferable is that the protruding portion 42 is not positioned distal to the ultrasound vibrator 31 in the in-plane direction D and the entire direction orthogonal to the extension direction A (hereinafter, referred to as "width direction E"). Thus, in the top view of FIG. 5, the protruding portion 42 of the present embodiment has parts positioned distal to the ultrasound vibrator 31 in both end portions in the width direction E, and a configuration lacking such a part is preferable. In this manner, the ultrasound vibrator 31 receiving ultrasound that becomes noise from the distal side can be further suppressed. Further, as illustrated in FIG. 7B, the protruding portion 42 may be positioned distal to the distal end 331e of the ultrasound vibrator 331 and only on the back surface side of the ultrasound transmitting/receiving surface 331a of the ultrasound vibrator 331.

Thus, the housing 32 of the present embodiment has a notch portion notched to the distal end 32a in a side view (see FIG. 4). Further, the ultrasound vibrator 31 is disposed in the notch portion.

More specifically, the protruding portion 42 is a concave plate portion curved in a circular arc shape in a cross section (see FIG. 6) in a direction orthogonal to the central axis direction parallel to the central axis of the proximal tubular portion 41 (direction substantially equal to the extension direction A in the sheath 23). Thus, the protruding portion 42 of the present embodiment is configured by a semi-tubular curved plate portion. The central axis of the proximal tubular portion 41 coincides with the central axis of the drive shaft 22 and substantially coincides with the central axis of the sheath 23 in the sheath 23. In the present embodiment, the central axis of the proximal tubular portion 41, the central axis of the drive shaft 22, and the central axis of the sheath 23 are all referred to as "central axis O". In FIG. 3, a gap is provided between the inner peripheral surface of the sheath 23 and the outer peripheral surface of the proximal tubular portion 41 of the housing 32 for convenience of explanation, and the gap can be practically almost nonexistent. Thus, the inner diameter of the first lumen 23a of the sheath 23 is substantially equal to the outer diameter of the proximal tubular portion 41 and the outer peripheral surface of the proximal tubular portion 41 abuts against the inner peripheral surface of the sheath 23 at a plurality of locations in the circumferential direction B or in the entire circumferential direction B.

As illustrated in FIG. 4, the position of the ultrasound vibrator 31 of the present embodiment is inside the outer peripheral surface of the proximal tubular portion 41 in the radial direction (direction substantially equal to the radial direction C in the sheath 23). Thus, the ultrasound vibrator 31 of the present embodiment does not protrude radially outward beyond the outer peripheral surface of the proximal tubular portion 41. In this manner, it is difficult for the ultrasound vibrator 31 to abut against the inner peripheral surface of the sheath 23 even when the outer peripheral surface of the proximal tubular portion 41 slides and rotates in relation to the inner peripheral surface of the sheath 23. Thus, the ultrasound vibrator 31 being damaged by abutting against the inner peripheral surface of the sheath 23 can be suppressed.

In addition, as illustrated in FIG. 4, end surfaces 42a on both sides of the concave plate portion as the protruding portion 42 of the present embodiment in the circumferential direction (direction substantially equal to the circumferential direction B in the sheath 23) extend so as to be inclined with respect to the central axis direction in a side view.

Further, as illustrated in FIG. 5, the proximal end surface of the ultrasound vibrator 31 is disposed at a position distally separated from the proximal tubular portion 41 in a top view. In this manner, the ultrasound transmitted from the ultrasound transmitting/receiving surface 31a of the ultrasound vibrator 31 being reflected by the proximal tubular portion 41 can be suppressed. As a result, the ultrasound transmitting/receiving surface 31a receiving the ultrasound that becomes noise reflected by the proximal tubular portion 41 can be suppressed. Further, an inclined distal end portion inclined with respect to the extension direction A may be formed at the distal end of the proximal tubular portion 41 in the circumferential region where the protruding portion 42 does not extend. The inclined distal end portion is inclined so as to approach the protruding portion 42 toward the distal side. In this manner, it becomes difficult for the ultrasound transmitted from the ultrasound transmitting/receiving surface 31a of the ultrasound vibrator 31 to reach the proximal tubular portion 41.

Examples of the material for the housing 32 can include metals such as stainless steel (SUS), a nickel-titanium alloy (Ni—Ti), and tungsten.

The backing member 33 is positioned between the protruding portion 42 and the ultrasound vibrator 31 and supports the ultrasound vibrator 31 from the back surface 31d side of the ultrasound transmitting/receiving surface 31a The backing member 33 is a sound-absorbing body made of, for example, rubber or epoxy resin in which metal powder such as tungsten powder is dispersed. By the backing member 33 being provided, partial ultrasound causing noise transmitted from the ultrasound vibrator 31 can be absorbed.

The backing member 33 of the present embodiment covers the entire back surface 31d of the ultrasound vibrator 31. As a result, the ultrasound transmitted from the back surface 31d of the ultrasound vibrator 31 can be absorbed. Further, the backing member 33 of the present embodiment is positioned on the proximal side of the ultrasound vibrator 31 and covers the proximal end surface of the ultrasound vibrator 31. Thus, the backing member 33 of the present embodiment is continuous not only on the back surface 31d side of the ultrasound vibrator 31, but also in the proximal tubular portion 41 and the entire proximal tubular portion 41 is filled with the backing member 33. As a result, the ultrasound transmitted from the proximal end surface of the ultrasound vibrator 31 can be absorbed.

Figure 8:
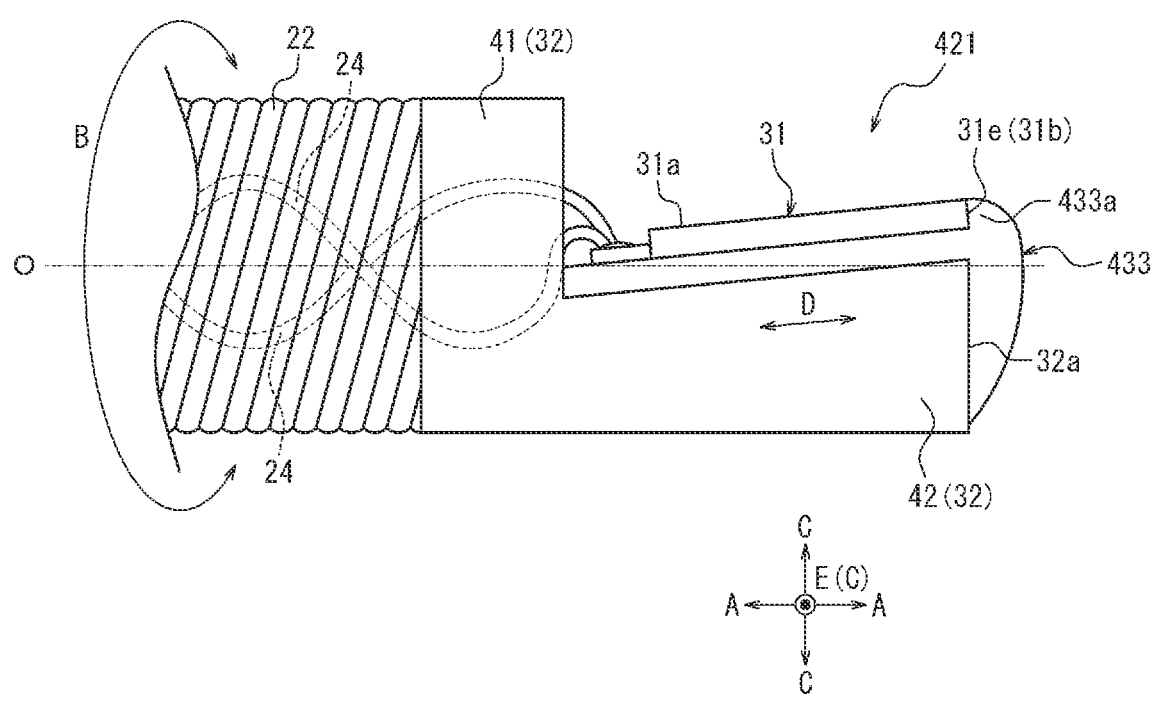
FIG. 8 is a diagram illustrating another modification example of the imaging core unit illustrated in FIG. 3.

The backing member 33 may cover the distal end surface 31b and the side end surface 31c of the ultrasound vibrator 31 without being limited to covering the back surface 31d of the ultrasound vibrator 31. In this manner, the ultrasound transmitted from the distal end surface 31b and the side end surface 31c of the ultrasound vibrator 31 can be absorbed by the backing member 33. Accordingly, partial ultrasound causing noise transmitted from the ultrasound vibrator 31 can be further absorbed. FIG. 8 is a diagram illustrating an imaging core unit 421 as a modification example of the imaging core unit 21. The imaging core unit 421 illustrated in FIG. 8 includes the ultrasound vibrator 31, the housing 32, and a backing member 433. Unlike the backing member 33 described above, the backing member 433 includes a distal cover portion 433a covering the distal end surface 31b of the ultrasound vibrator 31. Although the backing member 433 illustrated in FIG. 8 includes the distal cover portion 433a covering the distal end surface 31b of the ultrasound vibrator 31, the disclosure is not limited to this configuration and the backing member may include a side end cover portion covering the side end surface of the ultrasound vibrator in addition to or instead of the distal cover portion 433a.

In addition, the backing member 433 illustrated in FIG. 8 contains a scattering agent configured to scatter ultrasound (i.e., ultrasonic waves) upon the ultrasound striking the scattering agent. Examples of the scattering agent can include glass beads and polystyrene beads. By the distal cover portion 433a of the backing member 433 containing such a scattering agent, the ultrasound transmitting/receiving surface 31a receiving the ultrasound that becomes noise can be further suppressed by the ultrasound transmitted from the distal end surface 31b being scattered and the effect of absorbing ultrasound by means of the backing member 433 being achieved at the same time.

In addition, it is preferable that the backing member 433 does not protrude radially outward beyond the outer peripheral surface of the proximal tubular portion 41 of the housing 32 regardless of the presence or absence of the scattering agent. In this manner, the backing member 433 abutting against the inner peripheral surface of the sheath 23 (see FIG. 3) can be suppressed.

The imaging core unit 21 of the present embodiment will be described again with reference to FIGS. 4 and 6. As described above, the end surfaces 42a on both sides of the concave plate portion as the protruding portion 42 of the present embodiment in the circumferential direction are inclined with respect to the central axis direction and extend in a side view. In addition, as illustrated in FIG. 6, the backing member 33 of the present embodiment includes a main body portion 33c positioned in a concave portion 42b of the concave plate portion as the protruding portion 42 of the housing 32 and flange portions 33d protruding from the main body portion 33c and supported by the end surfaces 42a on both sides of the concave plate portion in the circumferential direction. Accordingly, when the main body portion 33c of the backing member 33 is loaded in the concave portion 42b, the flange portion 33d of the backing member 33 is supported by the end surface 42a and positioned. Thus, by the end surface 42a being used, the backing member 33 can be easily positioned with respect to the concave plate portion as the protruding portion 42. Further, as described above, the end surface 42a is inclined with respect to the central axis direction in a side view. Accordingly, a support surface 33b of the backing member 33 supporting the ultrasound vibrator 31 can be inclined with respect to the extension direction A by the flange portion 33d of the backing member 33 being supported by the end surface 42a and positioned. Accordingly, a state where the ultrasound transmitting/receiving surface 31a is inclined at a desired angle with respect to the extension direction A can be rather easily realized simply by the back surface 31d substantially parallel to the ultrasound transmitting/receiving surface 31a being placed on the support surface 33b of the backing member 33. Thus, the ultrasound transmitting/receiving surface 31a of the ultrasound vibrator 31 inclined at a desired angle can be rather easily realized.

Further, the side of the imaging core unit 21 faced by the ultrasound transmitting/receiving surface 31a is the upper side and the opposite side is the lower side. In this case, the protruding portion 42 is preferably positioned below the central axis O of the proximal tubular portion 41 in the side view illustrated in FIG. 4. In this manner, the position of the ultrasound vibrator 31 can be rather easily brought closer to the position of the central axis O of the drive shaft 22. The rotation of the ultrasound vibrator 31 can be stabilized by the position of the ultrasound vibrator 31 being brought closer to the position of the central axis O of the drive shaft 22. In addition, with such a configuration, the signal line 24 can be rather easily drawn into the drive shaft 22. In particular, the rotation of the ultrasound vibrator 31 can be further stabilized by the center position of the rotation of the ultrasound vibrator 31 being allowed to coincide with the position of the central axis O of the drive shaft 22. As illustrated in FIG. 4, in the present embodiment, the proximal ends of the end surfaces 42a on both sides of the concave plate portion as the protruding portion 42 in the circumferential direction are positioned below the central axis O of the proximal tubular portion 41 in a side view. Accordingly, as described above, the position of the ultrasound vibrator 31 can be rather easily aligned with the position of the central axis O of the drive shaft 22. Further, by the position of the ultrasound vibrator 31 being brought closer to the position of the central axis O of the drive shaft 22, a change in position attributable to rotation can be suppressed and a more accurate tomographic image of living tissue can be generated.

The concave portion 42b may not be entirely filled with the main body portion 33c. However, considering the performance of ultrasound absorption, a configuration in which the concave portion 42b is entirely filled is preferable.

In addition, by the backing member 33 including the flange portion 33d described above, the end surface 42a of the protruding portion 42 of the housing 32 can be covered with the flange portion 33d. As a result, the ultrasound transmitted from the ultrasound vibrator 31 being reflected by the end surface 42a of the protruding portion 42 of the housing 32 and received as ultrasound noise can be suppressed.

Figure 9:
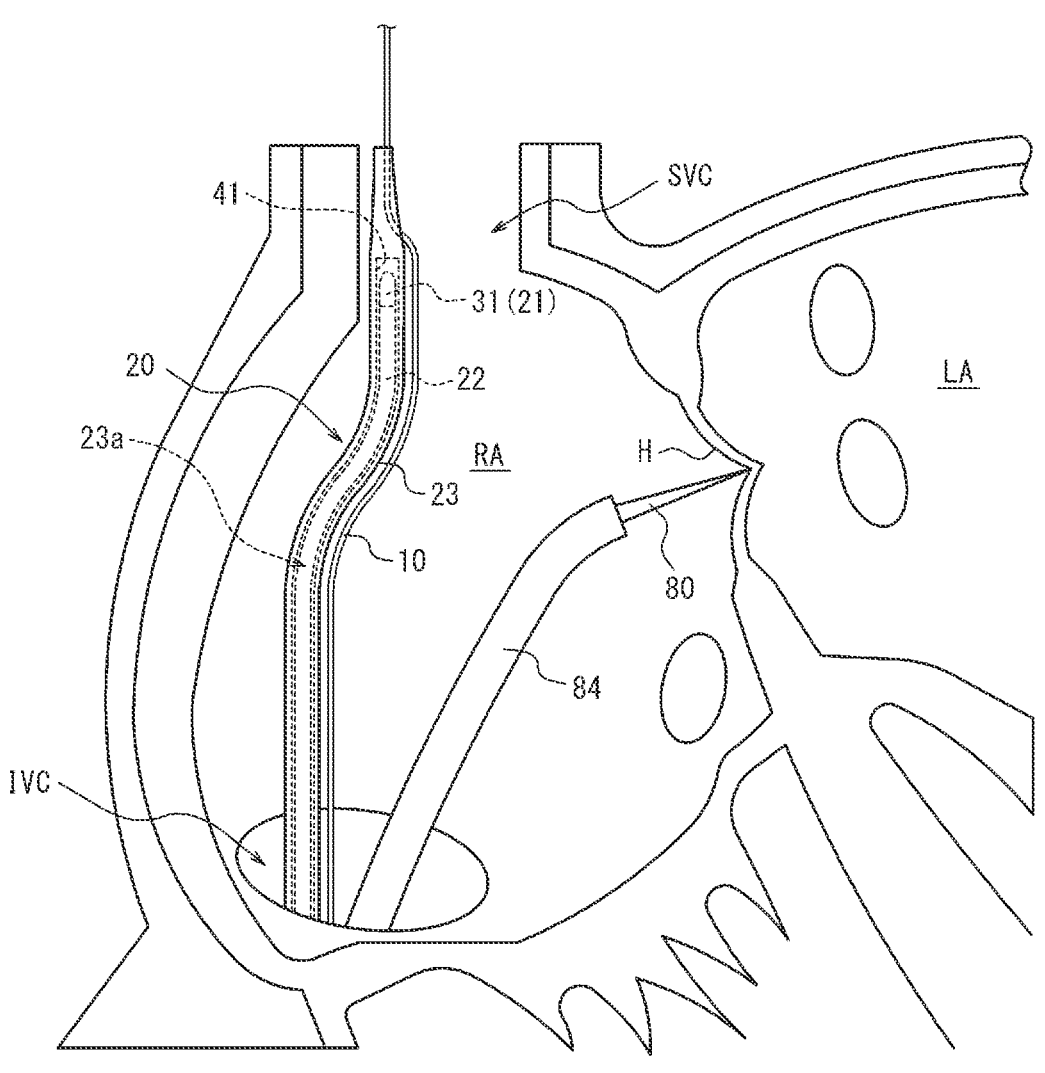
FIG. 9 is a diagram illustrating a state where the image diagnosis catheter illustrated in FIG. 2 is inserted through a right atrium of a heart.

Lastly, an example of a procedure performed by means of the image diagnosis catheter 20 of the present embodiment will be described with reference to FIG. 9. FIG. 9 illustrates the image diagnosis catheter 20 inserted through a right atrium RA of the heart. As illustrated in FIG. 9, an operator such as a medical worker inserts the image diagnosis catheter 20 into the right atrium RA via an inferior vena cava IVC as a first blood vessel smaller in diameter than the right atrium RA of a subject. At this time, the operator inserts a Brockenbrough needle 80 as a medical instrument positioned in the right atrium RA through a guiding catheter 84 into the right atrium RA via the inferior vena cava IVC. The Brockenbrough needle 80 is used for a left atrium LA to be opened from the right atrium RA through a foramen ovalis H isolating the right atrium RA and the left atrium LA from each other.

As illustrated in FIG. 9, the operator inserts the distal end portion of the image diagnosis catheter 20 into a superior vena cava SVC as a second blood vessel smaller in diameter than the right atrium RA communicating from the right atrium RA. Specifically, the distal end portion of the image diagnosis catheter 20 can be inserted into the superior vena cava SVC along the guide wire 10 after the guide wire 10 is inserted into the superior vena cava SVC. As a result, the vibration of the distal end portion of the image diagnosis catheter 20 can be suppressed. Further, the proximal side of the image diagnosis catheter 20 is in the inferior vena cava IVC smaller in diameter than the right atrium RA, and thus the image diagnosis catheter 20 extends over the superior vena cava SVC and the inferior vena cava IVC smaller in diameter than the right atrium RA and the vibration and movement of the part of the image diagnosis catheter 20 positioned in the right atrium RA are suppressed.

In addition, by the part of the image diagnosis catheter 20 positioned in the right atrium RA being curved, the first lumen 23a of the sheath 23 where the ultrasound vibrator 31 is accommodated can be curved. By the first lumen 23a being curved in this manner, the extension direction A of the sheath 23 can be changed and the position in the right atrium RA where the ultrasound vibrator 31 moves can be changed. Accordingly, a part (such as the foramen ovalis H of the heart) where observation is particularly needed on the inner wall surface of, for example, the organ or the like can be approached.

The ultrasound vibrator 31 moves in the extension direction A while rotating in the circumferential direction B in the first lumen 23a of the sheath 23. During the movement, the ultrasound vibrator 31 transmits ultrasound in the radial direction C and receives the ultrasound reflected by, for example, the inner wall surface of the right atrium RA. As a result, the ultrasound vibrator 31 acquires position information on the inner wall surface of the right atrium RA as surrounding information. Further, the ultrasound vibrator 31 acquires position information on the Brockenbrough needle 80 as a medical instrument positioned in the right atrium RA as surrounding information. Then, the control unit 54 generates a tomographic image reflecting the position information on the inner wall surface of the right atrium RA and the position information on the Brockenbrough needle 80 based on the surrounding information acquired by the ultrasound vibrator 31.

As described above, the ultrasound vibrator 31 is moved in the sheath 23 in a state where the vibration and movement of the part of the image diagnosis catheter 20 positioned in the right atrium RA are suppressed, and thus the rotation of the ultrasound vibrator 31 in the circumferential direction B and the movement of the ultrasound vibrator 31 in the extension direction A are stable. Accordingly, surrounding information such as the position information on the inner wall surface of the right atrium RA can be stably acquired. At this time, the storage unit 53 stores the tomographic image generated by the control unit 54 when the ultrasound vibrator 31 moves in the extension direction A and the position of the ultrasound vibrator 31 in the extension direction A at that time in association with each other at any time.

The control unit 54 may generate a three-dimensional image of the right atrium RA by superimposing tomographic images using the information stored in the storage unit 53.

As described above, the ultrasound vibrator 31 of the image diagnosis catheter 20 is inclined such that the ultrasound transmitting/receiving surface 31*a* (see FIG. 4 and so on) faces the proximal side. Accordingly, it becomes rather easy to acquire a tomographic image in which the tip position of the Brockenbrough needle 80 does not overlap another part of the Brockenbrough needle 80 by disposing the ultrasound vibrator 31 closer to the back side than the foramen ovalis H punctured by the Brockenbrough needle 80 as illustrated in FIG. 9 and generating a tomographic image proximal to the position of the ultrasound vibrator 31. Thus, by the ultrasound transmitting/receiving surface 31*a* (see FIG. 4 and so on) being configured to be inclined so as to face the proximal side, it becomes rather easy to acquire a tomographic image in which the tip position of a medical instrument inserted into a living body together with the image diagnosis catheter 20 and used is clear. This is not limited to the procedure illustrated in FIG. 9 and can be similarly applied to any procedure performed in a relatively wide space in a living body such as the atrium.

In addition, although the right atrium RA of the heart is illustrated as an example of the lumen of the organ or the like in FIG. 9, the lumen of the organ or the like into which the image diagnosis catheter 20 according to the disclosure is inserted is not particularly limited and the lumen may be, for example, the left atrium of the heart or the lumen of an organ other than the heart.

The detailed description above describes versions of an image diagnosis catheter representing examples of the inventive image diagnosis catheter disclosed here. The invention is not limited, however, to the precise embodiment and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An image diagnosis catheter comprising:
an elongated sheath configured to be inserted into a living body;
an imaging core unit disposed in the sheath;
a drive shaft attached to a proximal end of the imaging core unit and disposed in the sheath;
the imaging core unit including:
an ultrasound vibrator that includes an ultrasound transmitting/receiving surface, a back surface opposed to the ultrasound transmitting/receiving surface, and a distal end surface substantially orthogonal to the ultrasound transmitting/receiving surface, the ultrasound vibrator configured to transmit ultrasound from the ultrasound transmitting/receiving surface mainly toward a radial direction of the sheath orthogonal to an extension direction of the sheath; and a backing member that supports the back surface of the ultrasound vibrator and is configured to absorb a partial ultrasound transmitted from the ultrasound vibrator;
a housing configured to hold the ultrasound vibrator in the sheath;
wherein the drive shaft is movable with the imaging core unit in the sheath along the extension direction of the sheath and rotatable with the imaging core unit in the sheath around an axis of the sheath; and
the backing member includes a distal cover portion covering the distal end surface of the ultrasound vibrator, and a distal end of the housing does not cover the distal end surface of the ultrasound vibrator.

2. The image diagnosis catheter according to claim 1, wherein the housing is positioned distal to the distal end of the ultrasound vibrator and only on a back surface side of the ultrasound transmitting/receiving surface of the ultrasound vibrator.

3. The image diagnosis catheter according to claim 1, wherein the housing includes a proximal tubular portion disposed coaxially with the drive shaft and a protruding portion distally protruding from the proximal tubular portion and positioned on a back surface side of the ultrasound transmitting/receiving surface of the ultrasound vibrator.

4. The image diagnosis catheter according to claim 3, the protruding portion is positioned below a central axis of the proximal tubular portion in a case where a side faced by the ultrasound transmitting/receiving surface is an upper side and a lower side is opposite to the upper side.

5. The image diagnosis catheter according to claim 1,
wherein the ultrasound vibrator includes a side end surface substantially orthogonal to an ultrasound transmitting/receiving surface, the side end surface facing in a direction orthogonal to the extension direction of the sheath,
wherein the housing does not cover the side end surface of the ultrasound vibrator.

6. The image diagnosis catheter according to claim 1,
wherein the housing portion includes a concave plate portion extending along the extension direction of the sheath with being concaved outwardly in the radial direction of the sheath,
wherein the concave plate portion includes end surfaces on both sides of the concave plate portion, the end surfaces facing parallel to the ultrasound transmitting/receiving surface,
wherein the backing member further includes:
a main body portion disposed in a concave portion formed by the concave plate portion, and
a flange portion protruding from the main body portion and supported by the end surfaces of the concave plate portion in a circumferential direction of the sheath.

7. The image diagnosis catheter according to claim 1, the distal cover portion of the backing member includes a convex curved surface toward a distal direction.

* * * * *